(12) United States Patent
Higashi et al.

(10) Patent No.: US 11,091,432 B2
(45) Date of Patent: Aug. 17, 2021

(54) COMPOSITION, FLUORINATING REAGENT, AND METHOD FOR PRODUCING FLUORINATED ORGANIC COMPOUND

(71) Applicants: DAIKIN INDUSTRIES, LTD., Osaka (JP); National University Corporation Hokkaido University, Hokkaido (JP)

(72) Inventors: Masahiro Higashi, Osaka (JP); Yosuke Kishikawa, Osaka (JP); Shoji Hara, Sapporo (JP)

(73) Assignees: DAIKIN INDUSTRIES, LTD., Osaka (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 0 days.

(21) Appl. No.: 15/565,992

(22) PCT Filed: Apr. 19, 2016

(86) PCT No.: PCT/JP2016/062433
§ 371 (c)(1),
(2) Date: Oct. 12, 2017

(87) PCT Pub. No.: WO2016/171146
PCT Pub. Date: Oct. 27, 2016

(65) Prior Publication Data
US 2018/0111898 A1 Apr. 26, 2018

(30) Foreign Application Priority Data

Apr. 21, 2015 (JP) .............................. JP2015-087097

(51) Int. Cl.
| | |
|---|---|
| C07C 319/20 | (2006.01) |
| C07B 39/00 | (2006.01) |
| C07C 323/12 | (2006.01) |
| C01B 7/24 | (2006.01) |
| C07D 213/04 | (2006.01) |

(52) U.S. Cl.
CPC .......... *C07C 319/20* (2013.01); *C07B 39/00* (2013.01); *C07C 323/12* (2013.01); *C01B 7/24* (2013.01); *C07D 213/04* (2013.01)

(58) Field of Classification Search
CPC ......... C07C 319/20; C07B 39/00; C01B 7/24; C07D 213/04
See application file for complete search history.

(56) References Cited

U.S. PATENT DOCUMENTS

2004/0245505 A1* 12/2004 Yoneda .................. C07B 39/00
252/372
2012/0035329 A1 2/2012 Isogai et al.

FOREIGN PATENT DOCUMENTS

| DE | 10065218 A1 * | 7/2002 | ............. C07B 39/00 |
| JP | 09-309847 | 12/1997 | |
| JP | 2006-151894 | 6/2006 | |
| WO | 2010/113864 | 10/2010 | |

OTHER PUBLICATIONS

Wiezevich et al. ("Halogenated Hydrocarbon Solvents", Chemical Reviews, vol. 19, No. 2, pp. 101-117, Jul. 1936).*
Christian Reichardt, "Solvent Effects in Organic Chemistry", Department of Chemistry, Phillips University, Marburg, Federal Republic of Germany, 1984, pp. 21-40.*
T.W. Graham Solomons, 4th edition of Organic Chemistry, pp. 111-113 (Year: 1988).*
Richard J. Lewis, Sr., 12th edition of Hawley's Condensed Chemical Dictionary, pp. 128, 129, 266, 267, 336 and 1076. (Year: 1993).*
International Search Report dated Aug. 2, 2016 in International (PCT) Application No. PCT/JP2016/062433.
Kunigami et al., "Synthesis of fluoromethyl ethers and fluoromethyl esters by the reaction of the corresponding methylthiomethyl ethers and methylthiomethyl esters with $IF_5$—pyridine-HF", Journal of Fluorine Chemistry, vol. 167, Jun. 4, 2014, pp. 101-104.
Hara et al., "$IF_5$—pyridine-HF: air- and moisture-stable fluorination reagent", Tetrahedron, vol. 68, Oct. 2, 2012, pp. 10145-10150.
Extended European Search Report dated Nov. 7, 2018 in European Application No. 16783167.6.

* cited by examiner

*Primary Examiner* — Rosalynd A Keys
(74) *Attorney, Agent, or Firm* — Wenderoth, Lind & Ponack, L.L.P.

(57) ABSTRACT

An object of the present invention is to provide a method for producing a fluorinated organic compound with a high yield without using carbon tetrachloride in view of the fact that the production of a fluorinated organic compound with a sufficient yield was impossible for a hitherto-known method that uses a fluorinating agent that contains $IF_5$-pyridine-HF alone. Another object of the present invention is to provide a fluorinating reagent that is capable of achieving this object. The present invention provides a composition comprising (1) $IF_5$ and (2) an aprotic solvent (with the proviso that carbon tetrachloride is excluded), wherein the aprotic solvent is contained in an amount within a range of 50 mass ppm to 20 mass %.

16 Claims, No Drawings

COMPOSITION, FLUORINATING REAGENT, AND METHOD FOR PRODUCING FLUORINATED ORGANIC COMPOUND

TECHNICAL FIELD

The present invention relates to a composition, a fluorinating reagent, and a method for producing a fluorinated organic compound.

BACKGROUND ART

Fluorine compounds are extremely important for use as various chemical products, such as functional materials, compounds for medicines and agrochemicals, and electronic materials, and as intermediates of these chemical products, etc.

Fluoride, hydrogen fluoride, sulfur tetrafluoride, etc., have been used as fluorinating agents to obtain target fluorine compounds by fluorinating various organic compounds used as a starting material. These fluorinating agents, however, are difficult to handle due to their toxicity, corrosiveness, explosion risk at the time of reaction, etc., and thus require special devices or techniques.

A reaction for introducing a fluorine atom into an organic compound by utilizing nucleophilic substitution with a fluoride ion has recently been developed, as well as various fluorinating agents for use in this reaction.

For example, iodine pentafluoride ($IF_5$) is known as a powerful fluorinating agent with high oxidizability. $IF_5$, however, is a dangerous liquid fluorinating agent because it reacts with moisture in air and decomposes while generating HF. There have recently been reports stating that mixing $IF_5$, which has such characteristics, with pyridine-HF yields in air a stable white solid ($IF_5$-pyridine-HF), which is effective for fluorinating various sulfur compounds, etc. (see Non-patent Literature 1 and Non-patent Literature 2).

CITATION LIST

Non-Patent Literature

Non-patent Literature 1: S. Hara, M. Monoi, R. Umemura, C. Fuse, Tetrahedron, 2012, 68, 10145-10150.

Non-patent Literature 2: Journal of Fluorine Chemistry, Volume 167, 2014, Pages 101-104

SUMMARY OF INVENTION

Technical Problem

Although $IF_5$-pyridine-HF is an excellent fluorinating agent, some fluorinated organic compounds cannot be produced with a sufficient yield by a method for producing a fluorinated organic compound using a fluorinating agent containing $IF_5$-pyridine-HF alone. Accordingly, an improved method for producing a fluorinated organic compound and an improved fluorinating agent are desired.

In the technique disclosed in Non-patent Literature 1, carbon tetrachloride is used as a solvent. According to industrial regulations, the carbon tetrachloride must be completely removed.

However, the study of the present inventors revealed that a fluorinated organic compound cannot be produced with a sufficient yield if carbon tetrachloride is completely removed.

Therefore, an object of the present invention is to provide a method for producing a fluorinated organic compound with a high yield without using carbon tetrachloride in view of the fact that the production of a fluorinated organic compound with a sufficient yield was impossible for a previously known method that uses a fluorinating agent that contains $IF_5$-pyridine-HF alone. Another object of the present invention is to provide a fluorinating reagent that is capable of achieving the above object.

Solution to Problem

As a result of extensive research, the present inventors found that the above objects can be achieved with the use of a compound comprising:
(1) $IF_5$ and
(2) at least one aprotic solvent selected from the group consisting of (cyclo)alkanes, chlorine-containing organic solvents (with the proviso that carbon tetrachloride is excluded), aromatic solvents, nitrile-containing organic solvents, and fluorine-containing organic solvents,
wherein the solvent is contained in an amount within a range of 50 mass ppm to 20 mass %. Based on the above findings, the inventors conducted further research. The present invention has thus been accomplished.

The present invention encompasses the following embodiments.

Item 1. A composition comprising:
(1) $IF_5$ and
(2) at least one aprotic solvent selected from the group consisting of (cyclo)alkanes, chlorine-containing organic solvents, with the proviso that carbon tetrachloride is excluded, aromatic solvents, nitrile-containing organic solvents, and fluorine-containing organic solvents, wherein the aprotic solvent is contained in an amount within a range of 50 mass ppm to 20 mass %.

Item 2. The composition according to Item 1, further comprising an acid and a base.

Item 3. The composition according to Item 1, further comprising HF and an organic base.

Item 4. The composition according to Item 1, the composition comprising:
(1) $IF_5$-pyridine-HF and
(2) at least one aprotic solvent selected from the group consisting of (cyclo)alkanes, chlorine-containing organic solvents, with the proviso that carbon tetrachloride is excluded, aromatic solvents, nitrile-containing organic solvents, and fluorine-containing organic solvents,
wherein the aprotic solvent is contained in an amount within a range of 50 mass ppm to 20 mass %.

Item 5. The composition according to any one of Items 1 to 4, wherein the aprotic solvent is at least one member selected from the group consisting of (cyclo)alkanes, $C_1$ or $C_2$ chlorine-containing organic solvents, and fluorine-containing organic solvents.

Item 6. The composition according to any one of Items 1 to 4, wherein the aprotic solvent is a $C_{1-10}$ (cyclo)alkane.

Item 7. The composition according to any one of Items 1 to 4, wherein the aprotic solvent is cyclohexane.

Item 8. The composition according to any one of Items 1 to 7, which is a fluorinating reagent.

Item 9. A method for producing a fluorinated organic compound,
the method comprising Step A of fluorinating an organic compound by bringing the organic compound into contact with the composition of any one of Items 1 to 8.

The following describes in detail the composition, fluorinating reagent, and method for producing a fluorinated organic compound of the present invention.

Terms

The symbols and abbreviations used in this specification should be interpreted to have meanings that are usually used in the technical field to which the present invention belongs, and in a manner consistent with the context of this specification, unless otherwise stated.

In this specification, the term "comprise" or "contain" encompasses the meanings of "consist essentially of" and "consist of."

Composition

The composition of the present invention comprises:
(1) $IF_5$ and
(2) at least one aprotic solvent selected from the group consisting of (cyclo)alkanes, chlorine-containing organic solvents (with the proviso that carbon tetrachloride is excluded), aromatic solvents, nitrile-containing organic solvents, and fluorine-containing organic solvents. In this composition, the aprotic solvent is contained in an amount within a range of 50 mass ppm to 20 mass %.

In this specification, the chlorine-containing organic solvent refers to an organic solvent that contains one or more chlorine atoms as constituent atoms.

In this specification, the fluorine-containing organic solvent refers to an organic solvent that contains one or more fluorine atoms as constituent atoms.

Accordingly, the chlorine-containing organic solvents and the fluorine-containing organic solvents have overlapping concepts.

Examples of the (cyclo)alkanes as the aprotic solvent contained in the composition of the present invention include
(1) alkanes, such as pentane, hexane, and heptane; and
(2) cycloalkanes, such as cyclohexane and methylcyclohexane.

Examples of the chlorine-containing organic solvents as the aprotic solvent contained in the composition of the present invention include:
(1) chlorine-containing aliphatic solvents, such as dichloromethane, dichloroethane, chloroform, fluorotrichloromethane, 1,1,2-trichlorotrifluoroethane, 2-chloro-1,2-dibromo-1,1,2-trifluoroethane, 1,1-difluorotetrachloroethane, 1,2-difluorotetrachloroethane, heptafluoro-2,3,3-trichlorobutane, 1,1,1,3-tetrachlorotetrafluoropropane, 1,1,1-trichloropentafluoropropane, 1,1,1-trichlorotrifluoroethane, and polychlorotrifluoroethylene; and
(2) chlorine-containing aromatic solvents, such as chlorobenzene and dichlorobenzene.

Examples of the fluorine-containing organic solvents as the aprotic solvent contained in the composition of the present invention include:
(1) fluorotrichloromethane, 1,1,2-trichlorotrifluoroethane, 2-chloro-1,2-dibromo-1,1,2-trifluoroethane, 1,2-dibromohexafluoropropane, 1,2-dibromotetrafluoroethane, 1,1-difluorotetrachloroethane, 1,2-difluorotetrachloroethane, heptafluoro-2,3,3-trichlorobutane, 1,1,1,3-tetrachlorotetrafluoropropane, 1,1,1-trichloropentafluoropropane, and 1,1,1-trichlorotrifluoroethane; and
(2) fluorine-containing aliphatic solvents, such as polychlorotrifluoroethylene, and fluorine-containing aromatic solvents, such as fluorobenzene.

Examples of the aromatic solvents as the aprotic solvent contained in the composition of the present invention include benzene, toluene, chlorobenzene, and the like.

Examples of the nitrile-containing organic solvents as the aprotic solvent contained in the composition of the present invention include acetonitrile, propionitrile, benzonitrile, and the like.

These aprotic solvents may be used alone or in a combination of two or more.

Carbon tetrachloride is excluded from the aprotic solvents. It is preferable that the composition of the present invention is substantially or completely free of carbon tetrachloride.

The aprotic solvent is preferably a nonpolar solvent.

The aprotic solvent is preferably at least one member selected from the group consisting of (cyclo)alkanes, chlorine-containing organic solvents (with the proviso that carbon tetrachloride is excluded), and fluorine-containing organic solvents.

The aprotic solvent is preferably at least one member selected from the group consisting of $C_{1-10}$ (cyclo)alkanes, $C_1$ or $C_2$ chlorine-containing organic solvents (more preferably chloroform), and fluorine-containing organic solvents.

The aprotic solvent is preferably a $C_{1-10}$ (cyclo)alkane.

More specifically, the aprotic solvent is particularly preferably at least one member selected from the group consisting of cyclohexane, hexane, heptane, dichloromethane, and chloroform.

The aprotic solvent is most preferably cyclohexane.

The lower limit of the amount of the aprotic solvent contained in the composition of the present invention is preferably 50 mass ppm, more preferably 60 mass ppm, still more preferably 70 mass ppm, and even more preferably 80 mass ppm.

With this amount of aprotic solvent, the composition of the present invention suitably functions as a fluorinating agent; in other words, the use of the composition of the present invention makes it possible to obtain a fluorinated organic compound with a high yield from an organic compound used as a starting material.

The upper limit of the amount of the aprotic solvent contained in the composition of the present invention is not particularly limited, and is, for example, 25 mass %, 20 mass %, 15 mass %, 10 mass %, 5 mass %, 1 mass %, or 1000 mass ppm.

With this upper limit of the amount of aprotic solvent, handling of the solvent and the reaction system becomes easy.

The amount of the aprotic solvent contained in the composition of the present invention is preferably within a range of 50 mass ppm to 25 mass %, more preferably within a range of 50 mass ppm to 1 mass %, still more preferably within a range of 60 mass ppm to 1000 mass ppm, even more preferably within a range of 70 mass ppm to 1000 mass ppm, and particularly preferably within a range of 80 mass ppm to 1000 mass ppm.

The amount of aprotic solvent contained in the composition of the present invention may be measured by using a commonly used method that is capable of accurately measuring the amount of the aprotic solvent. Specifically, the measurement may be performed by using the following method for measuring a solvent amount.

Method for Measuring a Solvent Amount
i) Accurately weigh about 50 to 150 mg of the composition of the present invention;
ii) Add 4 ml of 0.1N KOH aqueous solution;
iii) Add 2 ml of toluene;
iv) Stir the mixture for 5 minutes, and allow the resulting mixture to stand for 10 minutes;

v) Subject the solvent in the toluene layer to GC measurement; and vi) Calculate the solvent amount, based on the calibration curve value. The average value obtained with n=3 is considered the solvent amount. The "solvent amount" as used herein means the amount of the solvent contained in the composition of the present invention, i.e., (mass of the solvent)/(mass of the composition of the present invention).

The composition of the present invention preferably further comprises 1 to 4 members, and more preferably 1 to 3 members selected from the group consisting of acids, bases, salts, and additives. The composition of the present invention even more preferably further comprises 1 to 3 members selected from the above group excluding combinations of an acid, a basic and a salt.

Specific examples of the acids include sulfuric acid, nitric acid, phosphoric acid, polyphosphoric acid, hydrogen fluoride, fluoric acid, hydrochloric acid, hydrogen bromide, hydrogen iodide, hypochlorous acid, chlorous acid, chloric acid, perchloric acid, perbromic acid, periodic acid, and like hydrogen halides, hydrohalic acid, hypohalous acid, halous acid, halogen acid, and perhalogen acid;

fluorosulfonic acid, chlorosulfonic acid, methanesulfonic acid, ethanesulfonic acid, trifluoromethanesulfonic acid, difluoromethanesulfonic acid, trichloromethanesulfonic acid, perfluorobutanesulfonic acid, perfluorooctanesulfonic acid, benzenesulfonic acid, toluenesulfonic acid, nitrobenzenesulfonic acid, and like sulfonic acids, polystyrenesulfonic acid, fluorinated sulfonic acid resin (Nafion-H), and like polymer carrying sulfonic acids; formic acid, acetic acid, propionic acid, chloroacetic acid, bromoacetic acid, dichloroacetic acid, trichloroacetic acid, trifluoroacetic acid, glycolic acid, lactic acid, benzoic acid, oxalic acid, succinic acid, and like mono- or poly-carboxylic acids;

$SO_3$, $BF_3$, $BCl_3$, $B(OCH_3)_3$, $AlCl_3$, $AlBr_3$, $SbF_3$, $SbCl_3$, $SbF_5$, $PF_3$, $PF_5$, $AsF_3$, $AsCl_3$, $AsF_5$, $TiCl_4$, $NbF_5$, $TaF_5$, and like Lewis acids, and their ether complexes;

$HBF_4$, $HPF_6$, $HAsF_6$, $HSbF_6$, $HSbCl_6$, and like acids faulted of Lewis acids and hydrogen halides, and their ether complexes; and mixtures of two or more these members.

The acids used here may be supported by several kinds of carriers.

Examples of the carriers include $SiO_2$, methylated $SiO_2$, $Al_2O_3$, $Al_2O_3$—WB, $MoO_3$, $ThO_2$, $ZrO_2$, $TiO_2$, $Cr_2O_3$, $SiO_2$—$Al_2O_3$, $SiO_2$—$TiO_2$, $SiO_2$—$ZrO_2$, $TiO_2$—$ZrO_2$, $Al_2O_3$—$B_2O_3$, $SiO_2$—$WO_3$, $SiO_2$—$NR_4F$, $HSO_3Cl$—$Al_2O_3$, $HF$—$NH_4$—$Y$, $HF$—$Al_2O_3$, $NH_4F$—$SiO_2$—$Al_2O_3$, $AlF_3$—$Al_2O_3$, $Ru$—$F$—$Al_2O_3$, $F$—$Al_2O_3$, $KF$—$Al_2O_3$, $AlPO_4$, $AlF_3$, bauxite, kaolin, activated carbon, graphite, Pt-graphite, ion-exchange resins, metal sulfate, chloride, metals (e.g., Al), alloys (e.g., Al—Mg, Ni—Mo), polymers (e.g., polystyrene), and the like.

When the composition of the present invention contains an acid, the amount is preferably within a range of 0.5 to 20 mol, more preferably within a range of 0.8 to 10 mol, and even more preferably within a range of 0.9 to 5 mol, per mol of $IF_5$.

Examples of the base include sodium hydroxide, potassium hydroxide, lithium hydroxide, rubidium hydroxide, cesium hydroxide, magnesium hydroxide, calcium hydroxide, barium hydroxide, and like alkali metal hydroxides or alkaline earth metal hydroxides;

sodium methoxide, sodium ethoxide, sodium butoxide, potassium methoxide, potassium ethoxide, potassium butoxide, lithium methoxide, lithium ethoxide, and like alkali metal alkoxides; sodium hydride, potassium hydride, lithium hydride, calcium hydride, and like alkali metal hydrides or alkaline earth metal hydrides;

sodium, potassium, lithium, and like alkali metals; magnesium oxide, calcium oxide, and like alkaline earth metal oxides;

ammonia, ammonium hydroxide, tetramethylammonium hydroxide, tetraethylammonium hydroxide, tetrabuthylammonium hydroxide, octyltriethylammonium hydroxide, benzyltrimethylammonium hydroxide, and like ammonium hydroxide salts, amberlite resin, and like polymer carrying ammonium hydroxide salts, and the like; aliphatic amine (primary amine, secondary amine, tertiary amine), alicyclic amine (secondary amine, tertiary amine), aromatic amine (primary amine, secondary amine, tertiary amine), heterocyclic amine, and like organic bases; polyaryl amine, polyvinylpyridine, and like polymer carrying amine compounds; and the like.

In this specification, examples of aliphatic primary amines include methylamine, ethylamine, propylamine, butylamine, pentylamine, hexylamine, cyclohexylamine, ethylenediamine, and the like.

In this specification, examples of aliphatic secondary amines include dimethylamine, diethylamine, dipropylamine, dibutylamine, dipentylamine, dihexylamine, dicyclohexylamine, and the like.

In this specification, examples of aliphatic tertiary amines include trimethylamine, triethylamine, diisopropylethylamine, N,N,N',N'-tetramethylethylenediamine, and the like.

In this specification, examples of alicyclic secondary amines include piperidine, piperazine, pyrrolidine, morpholine, and the like.

In this specification, examples of alicyclic tertiary amines include N-methylpiperazine, N-methylpyrrolidine, 5-diazabicycio[4,3,0]nonan-5-ene, 1,4-diazabicyclo[2,2,2]octane, and the like.

In this specification, examples of aromatic amines include aniline, methylaniline, dimethylaniline, N,N-dimethylaniline, haloaniline, nitroaniline, and the like.

In this specification, examples of heterocyclic amines include pyridine, pyrimidine, piperazine, quinoline, imidazole, and the like.

When the composition of the present invention contains a base, the amount is preferably within a range of 0.5 to 20 mol, more preferably within a range of 0.8 to 10 mol, and still more preferably within a range of 0.9 to 5 mol, per mol of $IF_5$.

Examples of the additives include halogens, interhalogen compounds, polyhalides, and the like.

Specific examples of halogens include iodine, bromine, chlorine, and the like. Among those, iodine and bromine are preferable, and iodine is more preferable.

Specific examples of the interhalogen compounds include ClF, BrF, ICl, IBr, $I_2Cl_6$, $ICl_3$, and the like.

Specific examples of the polyhalides include $LiCl_4I$, $NaCl_4I$, $KCl_4I$, $CsCl_4I$, $RbCl_4I$, $Me_4NCl_4I$, $Et_4NCl_4I$, $Pr_4NCl_4I$, $Bu_4NCl_4I$, $PhNMe_3Cl_4I$, $PhCH_2NMe_3Cl_4I$, $Me_3SCl_4I$, $Cl_8IP$, $KCl_3I_2$, $Me_4NCl_3I_2$, 2,2-bipyridinium µ-chlorodichlorodiiodate, 2,2'-biguinolinium µ-chlorodichlorodiiodate, $KCl_2I$, $Me_4NCl_2I$, $Me_4NClI_2$, $Et_4NCl_3$, $Ph_4AsCl_3$, $KClF_2$, $Me_4NClF_4$, $CsClF_4$, $CsCl_3FI$, $KBrClI$, $NH_4BrClI$, $Me_4NBrClI$, $Me_4NBrCl_2$, $Bu_4NBrCl_2$, $Me_4NBrCl_2I_2$, $CsBrFI$, $NaBrF_2$, $KBrF_2$, $CsBrP_4$, $Me_4NBrF_4$, $CsBrF_6$, $Me_4NBrF_6$, $Et_4NBr_6Cl$, $CsBr_3$, $Me_4NBr_3$, $Et_4Br_3$, $Bu_4NBr_3$, $PhCH_2NMe_3Br_3$, pyridinium tribromide, $Br_7P$, $CsBrI_2$, $Me_4NBrI_2$, $Me_4NBrI_4$, $Me_4NBrI_6$, $KBr_2Cl$, $Me_4NBr_2Cl$, $Bu_4NBr_2Cl$, $KBr_2I$, $Me_4NBr_2I$, $Bu_4NBr_2I$, 2,2'-bipyridinium μ-bromodibromodiiodate, $NaF_2I$, $KF_2I$, $CSF_4I$, $CsF_6I$, $CsF_8I$, $KI_3$, $CsI_3$, $Me_4NI_3$, $Et_4NI_3$, $Pr_4NI_3$, $Bu_4NI_3$, pyridinium triiodide, $Me_4NI_5$, $Et_4NI_7$, $Me_4NI_9$, $Me_4PBr_3$, $Me_4PI_3$, $Me_4PIBr_2$, $Me_4PICl_2$, $Et_4PI_3$, $Bu_4PI_3$, $Ph_4PI_3$, $Ph_4PBr_3$, $Ph_4PIBr_2$, and the like.

These additives may be used alone or in a combination of two or more.

The composition of the present invention preferably contains an acid and a base.

When the composition of the present invention contains an acid and a base, the acid and the base may exist as a salt in the composition of the present invention.

Examples of the salt include sodium sulfate, sodium hydrogensulfate, potassium sulfate, potassium hydrogensulfate, lithium sulfate, cesium sulfate, calcium sulfate, magnesium sulfate, ammonium sulfate, triethylammonium sulfate, pyridinium sulfate, trimethylpyridinium sulfate, polyarylammonium sulfate, polyvinylpyridinium sulfate, sodium methanesulfonate, ammonium methanesulfonate, tetramethylammonium methanesulfonate, potassium ethanesulfonate, lithium butanesulfonate, sodium benzenesulfonate, sodium toluenesulfonate, sodium trifluoromethanesulfonate, sodium polystyrenesulfonate, and like metal salts or ammonium salts of sulfuric acids or sulfonic acids; sodium formate, ammonium formate, sodium acetate, potassium acetate, lithium acetate, magnesium acetate, calcium acetate, ammonium acetate, methylammonium acetate, diethylammonium acetate, triethylammonium acetate, tetraethylammonium acetate, pyridinium acetate, sodium propionate, potassium propionate, sodium butyrate, polyarylammonium acetate, polyvinylpyridinium acetate, sodium isobutyrate, sodium valerianate, sodium nonanoate, sodium chloroacetate, sodium bromoacetate, sodium trichloroacetate, sodium trifluoroacetate, sodium glycolate, sodium lactate, sodium benzoate, sodium oxalate, sodium succinate, sodium polyacrylate, and like metal salts or ammonium salts of carboxylic acids; LiBr, LiI, NaBr, NaI, KBr, KI, RbBr, RbI, CsBr, CsI, $BeBr_2$, $BeI_2$, $MgBr_2$, $MgI_2$, $CaBr_2$, $CaI_2$, $SrBr_2$, $SrI_2$, $BaBr_2$, $BaI_2$, $ZnBr_2$, $ZnI_2$, $CuBr_2$, $CuI_2$, CuBr, CuI, AgBr, AgI, AuBr, AuI, $NiBr_2$, $NiI_2$, $PdBr_2$, $PdI_2$, $PtBr_2$, $PtI_2$, $CoBr_2$, $CoI_2$, $FeBr_2$, $FeBr_3$, $FeI_2$, $FeI_3$, $MnBr_2$, $MnI_2$, $CrBr_2$, $CrI_2$, $PbBr_2$, $PbI_2$, $SnBr_2$, $SnI_2$, $SnBr_4$, $SnI_4$, and like metal salts;
$NH_4Br$, $NH_4I$, $MeNH_3Br$, $MeNH_3I$, $Me_4NBr$, $Me_4NI$, $Et_4NBr$, $Et_4NI$, $Bu_4NBr$, $Bu_4NI$, $PhMe_3NBr$, $PhMe_3NI$, $PhCH_2NMe_3I$, pyridinium bromide, pyridinium iodide, chloropyridinium iodide, methylpyridinium iodide, cyanopyridinium iodide, bipyridinium iodide, quinolium iodide, isoquinolium iodide, N-methylpyridinium bromide, N-methylpyridinium iodide, N-methylquinolium iodide, and like pyridinium salts or ammonium salts;
$Me_4PBr$, $Me_4PI$, $Et_4PI$, $Pr_4I$, $Bu_4PBr$, $Bu_4PI$, $Ph_4PBr$, $Ph_4PI$, and like phosphonium salts;
sodium fluoride, potassium fluoride, cesium fluoride, ammonium fluoride, tetraethylammonium fluoride, tetrabutylammonium fluoride, polyarylammonium fluoride, sodium chloride, ammonium chloride, sodium hypochlorite, sodium chlorite, sodium chlorate, sodium perchlorate, sodium perbromate, sodium periodate, and like metal salts or amine salts of hydrogen halides, hypohalous acids, halous acids, halogen acids, or perhalogen acids;
sodium carbonate, potassium carbonate, lithium carbonate, sodium hydrogencarbonate, potassium hydrogencarbonate, lithium hydrogencarbonate, calcium carbonate, magnesium carbonate, and like carbonates;
sodium phosphate, potassium phosphate, sodium hydrogenphosphate, sodium dihydrogenphosphate, ammonium phosphate, pyridinium phosphate, and like metal salts or amine salts of phosphoric acids;
sodium nitrate, potassium nitrate, ammonium nitrate, pyridinium nitrate, and like metal salts or amine salts of nitric acid; $NaBF_4$, $KBF_4$, $LiBF_4$, $NaSbF_6$, $NaAsF_6$, $NaPF_6$, $NH_4BF_4$, $NH_4SbF_6$, $NH_4PF_6$, and like metal salts or amine salts formed of Lewis acids and hydrogen halides;
tetramethylphosphonium fluoride, tetramethylphosphonium acetate, tetraphenylphosphonium fluoride, and like phosphonium salts; $(C_2H_5)_4NF$, 1-ethyl-3-methylimidazolium fluoride, $(C_2H_5)_3N—(HF)_n$, $(C_2H_5)_4NF—(HF)_n$, $(n-C_4H_9)_3N—(HF)_n$, $(n-C_4H_9)_4NF—(HF)_n$, $BF_3 \cdot Et_2O—(HF)_n$, and like room temperature molten salts having fluoride anions or HF, wherein n=1 to 20.

These salts may be used alone or in a combination of two or more.

The composition of the present invention particularly preferably contains HF as an acid and pyridine as a base.

In the composition of the present invention, $IF_5$ may be complexed with an acid and a base.

In the composition of the present invention, some or all (preferably substantially all, and more preferably all) of $IF_5$, HF, and pyridine are present as $IF_5$-pyridine-HF.

$IF_5$-pyridine-HF is a known substance disclosed in Non-Patent Literature 1.

$IF_5$-pyridine-HF is a complex consisting of (1) $IF_5$, (2) 1 mol of pyridine per mol of $IF_5$, and (3) 1 mol of HF per mol of $IF_5$.

$IF_5$-pyridine-HF is generally produced in accordance with the method disclosed in Non-Patent Literature 1.

Specifically, $IF_5$-pyridine-HF is obtained by mixing $IF_5$ with pyridine-HF (pyridine 50 mol %, HF 50 mol %). Pyridine-HF (pyridine 50 mol %, HF 50 mol %) is obtained by adding pyridine to an equimolar amount of anhydrous HF.

In a preferable embodiment of the composition of the present invention, the composition comprises:
(1) $IF_5$-pyridine-HF, and
(2) at least one aprotic solvent selected from the group consisting of (cyclo)alkanes, chlorine-containing organic solvents (with the proviso that carbon tetrachloride is excluded), aromatic solvents, nitrile-containing organic solvents, and fluorine-containing organic solvents,
wherein the aprotic solvent is contained in an amount within a range of 50 mass ppm to 20 mass %.

The amount of "(1) $IF_5$-pyridine-HF" contained in the composition of this embodiment is preferably, for example, 80 mass % or more, 90 mass % or more, 95 mass % or more, 96 mass % or more, 97 mass % or more, 98 mass % or more, or 99 mass % or more.

As long as the effect of the present invention is not significantly impaired, the composition of the present invention may contain $IF_5$, pyridine, HF, or a combination thereof, which do not constitute $IF_5$-pyridine-HF. The amount thereof is preferably 45 mass % or less in total.

In addition, as long as the effect of the present invention is not significantly impaired, the composition of the present invention may contain water. The amount of water is preferably 1 mass % or less.

In a preferable embodiment of the composition of the present invention, the aprotic solvent may be complexd with the $IF_5$-pyridine-HF.

In a preferable embodiment of the composition of the present invention, the lower limit of the amount of the aprotic solvent is preferably 50 mass ppm, and more preferably 80 mass ppm.

With this amount of the aprotic solvent, the composition of the present invention according to this preferable embodiment suitably functions as a fluorinating agent; in other words, the use of the composition of the present invention according to this preferable embodiment makes it possible to obtain a fluorinated organic compound with a high yield from an organic compound used as a starting material.

The upper limit of the amount of the aprotic solvent contained in the composition of the present invention according to the preferable embodiment is not particularly limited, and is, for example, 20 mass %, 1 mass %, or 1000 mass ppm.

The amount of the aprotic solvent contained in the composition of the present invention according to the preferable embodiment is preferably within a range of 50 mass ppm to 20 mass %, more preferably within a range of 50 mass ppm to 1 mass %, and still more preferably within a range of 70 mass ppm to 1000 mass ppm.

Production Method for the Composition

The composition of the present invention may be produced by or according to the following method.

Hereinafter, "at least one aprotic solvent selected from the group consisting of (cyclo)alkanes, chlorine-containing organic solvents (with the proviso that carbon tetrachloride is excluded), aromatic solvents, nitrile-containing organic solvents, and fluorine-containing organic solvents" is sometimes simply referred to as "an aprotic solvent."

The following describes a method for producing a composition comprising:

(1) IF$_5$-pyridine-HF and
(2) an aprotic solvent,
wherein the aprotic solvent is contained in an amount within a range of 50 mass ppm to 20 mass %. However, the present invention is not limited to the following.

IF$_5$ is placed in a container, to which an aprotic solvent (e.g., cyclohexane) is added, followed by further addition of a mixture of pyridine-HF.

The resulting mixture is dried under reduced pressure so that the amount of the aprotic solvent is within the desired range.

Here, it is desirable that the amount of the aprotic solvent does not fall below the predetermined amount. When the amount of the aprotic solvent falls below the predetermined amount, even if the aprotic solvent is added so that the amount of the aprotic solvent satisfies the desired range, the obtained composition would not function as a fluorinating reagent with sufficiently high performance.

The composition of the present invention can be suitably used as a fluorinating reagent.

The composition of the present invention can be used as a fluorinating reagent that is used in the following method for producing a fluorinated organic compound.

Method for Producing a Fluorinated Organic Compound

The method for producing a fluorinated organic compound of the present invention comprises Step A of fluorinating an organic compound by bringing the organic compound into contact with the composition of the present invention.

In the present invention, examples of the organic compound, which is a reaction substrate, include:

(1) compounds having an OH group;
(2) ketones (including diketone, β-ketocarboxylic acid, and β-ketoester), ketoester), aldehydes, imines such as Schiff base and hydrazone, or esters;
(3) sulfides;
(4) epoxies;
(5) aromatic compounds (e.g., phenylhydrazine derivatives, phenol derivatives, 2-naphthol derivatives, and aniline derivatives);
(6) thiocarbonyl compounds; and
(7) unsaturated carbon compounds (e.g., olefin compounds).

The fluorination of organic compounds in the present invention includes replacement of a hydrogen atom with a fluorine atom, as well as replacement or substitution of the following atom or group with a fluorine atom as shown in each set of parentheses: hydrogen atom (CH→CF), carbonyl group (CO→CF$_2$), hydrazino group (C—NHNH$_2$→C—F; C=N—NH$_2$→CF$_2$), hydroxyl group (C—OH→C—F), and epoxy group (C—O—→C—F).

Fluorination conducted in the production method for the present invention is exemplified below. Fluorinated organic compounds obtained by the following production method for the present invention are also exemplified below.

(1) Fluorination of compounds having an OH group

In this fluorination, the following reactions, for example, are conducted.

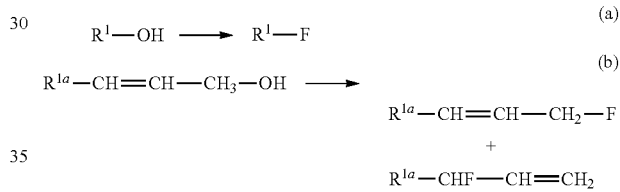

(In the above formulae, R$^1$ represents an alkyl group that may have at least one substituent, an aralkyl group that may have at least one substituent; an alkenyl group that may have at least one substituent, an acyl group, a cycloalkyl group that may have at least one substituent, or a heterocycloalkyl group that may have at least one substituent. R$^{1a}$ represents an alkyl group that may have at least one substituent, an aryl group that may have at least one substituent, an aralkyl group that may have at least one substituent, an alkenyl group that may have at least one substituent, an acyl group, a cycloalkyl group that may have at least one substituent, or a heterocycloalkyl group that may have at least one substituent).

In the present specification, "may have a substituent" includes both cases where a substituent is contained (i.e., substituted) and not contained (unsubstituted). For example, an alkyl group that may have at least one substituent includes alkyl groups (i.e., unsubstituted alkyl groups) and alkyl groups having a substituent (i.e., substituted alkyl groups).

Specific examples of compounds having an OH group include:

alcohols including aliphatic alcohols, such as methanol, ethanol, n-propanol, isopropanol, n-butanol, isobutanol, tert-butanol, pentanol, hexanol, octanol, decanol, palmityl alcohol, stearyl alcohol, and oleyl alcohol; alicyclic alcohols, such as benzyl alcohol, a mono-, di- or tri-saccharide having at least one non-protected hydroxyl group, cyclohexyl alcohol; and ascorbic acid; steroid alcohols, such as cholesterol, cholic acid, and cortisone; and carboxylic acids including aliphatic monocarboxylic acids, such as acetic acid, trifluoroacetic acid, propionic acid, acrylic acid, methacrylic acid, crotonic acid, butyric acid, valeric acid, isovaleric acid, pivalic acid, lauric acid, myristic acid, palmitic acid, stearic acid, oleic acid, linoleic acid, linolenic acid, and cinnamic acid; polycarboxylic acids, such as oxalic acid, succinic acid, malonic acid, glutaric acid, adipic acid, maleic acid, fumaric acid, and citric acid; aromatic carboxylic acids, such as benzoic acid, salicylic acid, (o-,m-,p-)phthalic acid, nalidixic acid, and nicotinic acid; vitamins having carboxylic acid groups, such as pantothenic acid and biotin; 20 kinds of natural amino acids, such as glycine, alanine, phenylalanine, cysteine, aspartic acid, glutamic acid, threonine, histidine, lysine, methionine, and proline; and hydroxycarboxylic acids, such as lactic acid, citric acid, malic acid, and tartaric acid.

(2) Fluorination of ketones (including diketone, β-ketocarboxylic acid, β-ketoester), aldehydes, imines such as Schiff base and hydrazone, and esters In this fluorination, the following reactions, for example, are conducted.

$$R^2-CH_2-C(=X)-R^{2a} \rightarrow R^2-CHF-C(=X)-R^{2a} \rightarrow R^2-CF_2-C(=X)-R^{2a} \quad (a\text{-}1)$$

$$H-CH_2-C(=X)-R^{2a} \rightarrow H-CHF-C(=X)-R^{2a} \rightarrow H-CF_2-C(=O)-R^{2a} \quad (a\text{-}2)$$

$$R^2-CH_2-C(=X)-H \rightarrow R^3-CHF-C(=X)-H \rightarrow R^2-CF_2-C(=X)-H \quad (a\text{-}3)$$

$$R^2-C(=X)-CH_2-C(=O)-R^{2a} \rightarrow R^2-C(=X)-CF_2-C(=X)-R^{2a} \quad (b\text{-}1)$$

$$H-C(=X)-CH_2-C(=X)-R^{2a} \rightarrow H-C(=X)-CHF-C(=X)-R^{2a} \rightarrow H-C(=X)-CF_2-C(=X)-R^{2a} \quad (b\text{-}2)$$

$$R^2-C(=X)-R^{2a} \rightarrow R^2-CF_2-R^{2a}(R^2)_2CH-COOR^{2b} \rightarrow (R^2)_2CF-COOR^{2b} \quad (c)$$

$$R^2-C(=N-NHR^{2c})-R^{3a} \rightarrow R^2-CF(-N=NR^{2c})-R^{2a} \rightarrow R^2-CF_2-R^{2a} \quad (d\text{-}1)$$

$$HC(=N-NHR^2)-R^{2a} \rightarrow F_2C(-N=NR^2)-R^{2a} \rightarrow CF_3-R^{2a} \quad (d\text{-}2)$$

(In the above formulae, X represents O or NR' (R' represents a hydrogen atom, an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, a heterocyclic group that may have at least one substituent, an alkoxy group that may have at least one substituent, an aryloxy group that may have at least one substituent, an amino group, a monoalkylamino group that may have at least one substituent, a dialkylamino group that may have at least one substituent, an acyl group, or an acylamino group. $R^2$, $R^{2a}$, and $R^{2c}$ may be the same or different, and each represents a hydrogen atom, an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, a heterocyclic group that may have at least one substituent, an alkoxy group that may have at least one substituent, an aryloxy group that may have at least one substituent, a monoalkylamino group that may have at least one substituent, a dialkylamino group that may have at least one substituent, an acyl group, or an acylamino group. $R^2$ and $R^{2a}$ taken together may form a ring structure.

$R^{2b}$ represents an alkyl group that may have at least one substituent, an aralkyl group that may have at least one substituent, or an aryl group that may have at least one substituent).

Examples of the ring structure include aliphatic 4- to 7-membered rings that may have at least one substituent.

Examples of ketones include acetone, methyl ethyl ketone, acetylacetone, acetoacetic acid, acetoacetate, cyclohexanone, acetophenone, benzophenone, propiophenone, 4-piperidone, 1-oxo-1,2-dihydronaphthalene, benzylideneacetophenone (chalcone), deoxybenzoin, ketals thereof, and the like.

Examples of aldehydes include acetoaldehyde, propionaldehyde, butylaldehyde, isobutylaldehyde, valeraldehyde, isovaleraldehyde, acrylaldehyde, benzaldehyde, cinnamaldehyde, anisaldehyde, nicotinealdehyde, acetals thereof, and the like.

Examples of imines, such as a Schiff base and hydrazone, include condensates of ketone or aldehyde with an appropriate primary amine or hydrazine.

Examples of esters include methyl isobutyrate, ethyl isobutylate, and the like.

(3) Fluorination of sulfides (including dithioacetal and dithioketal)

In this fluorination, for example, one or two hydrogen atoms of methylene that is located adjacent to a sulfur atom are substituted with fluorine atoms, or a sulfur atom is substituted with fluorine.

$$R^3-CH_2-S-R^{3a} \rightarrow R^3-CFH-S-R^{3a} \rightarrow R^3-CF_2-S-R^{3a} \quad (a\text{-}1)$$

$$R^3-CHR^{3b}-S-R^{3a} \rightarrow R^3-CFR^{3b}-SR^{3a} \quad$$

$$R^3-CO-CH_2-S-R^{3a} \rightarrow R^3-CO-CFH-S-R^{3a} \rightarrow R^3-CO-CF_2-S-R^{3a} \quad (b\text{-}1)$$

$$R^3-CO-CHR^{3b}-S-R^{3a} \rightarrow R^3-CO-CFR^{3b}-S-R^{3a} \quad (b\text{-}2)$$

$$R^{3c}R^{ad}C=C(SR^{3a})_2 \rightarrow R^{3c}R^{3d}CH-CF_2-SR^{3a} \rightarrow R^{3c}R^{3d}CH-CF_3 \quad (c)$$

$$R^{3c}R^{3d}C(SR^{3a'})(SR^{3a''}) \rightarrow R^{3c}R^{3d}CF_2 \quad (d)$$

$$R^3-C(SR^{3a})(SR^{3a'})(SR^{3a''}) \rightarrow R^3-CF_3 \quad (e)$$

$$R^3-C(SR^{3a})(SR^{3a'})-S-R^{3e}-S-(SR^{3a'})-(SR^{3a})-R^3 \rightarrow R^3-CF_3 \quad (f)$$

(In the above formulae, $R^{3a}$, $R^{3a'}$, and $R^{3a''}$ may be the same or different, and each represents an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, or a heterocyclic group that may have at least one substituent. Alternatively, $R^{3a}$ and $R^{3a'}$ taken together may form an aliphatic 4- to 7-membered ring that may have at least one substituent. $R^3$ and $R^{3b}$ may be the same or different, and each represents an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, a heterocyclic group that may have at least one substituent, an alkoxy group that may have at least one substituent, an aryloxy group that may have at least one substituent, an amino group, a monoalkylamino group that may have at least one substituent, a dialkylamino group that may have at least one substituent, an acyl group, an acylamino group, a cyano group, an alkylsulfinyl group that may have at least one substituent, an aralkylsulfinyl group that may have at least one substituent, an arylsulfinyl group that may have at least one substituent, a cycloalkylsulfinyl group that may have at least one substituent, a heterocycloalkylsulfinyl group that may have at least one substituent, a sulfinyl group bonded by a heterocyclic group that may have at least one substituent, an alkylsulfonyl group that may have at least one substituent, an aralkylsulfonyl group that may have at least one substituent, an arylsulfonyl group that may have at least one substituent, a cycloalkylsulfonyl group that may have at least one substituent, a heterocycloalkylsulfonyl group that may have at least one substituent, or a sulfonyl group bonded by a heterocyclic group that may have at least one substituent. Alternately, $R^3$ and $R^{3b}$ taken together with the carbon atom to which they are attached may form a 4- to 8-membered ring optionally via a hetero atom. (The ring may be substituted with at least one substituent selected from the group consisting of a halogen atom, an oxo group, an alkyl group that may have at least one substituent, an aralkyl group that may have at least one substituent, an aryl group that may have at least one substituent, an alkenyl group that may have at least one substituent, a cyano group, and an amino group.) $R^{3c}$ and $R^{3d}$ may be the same or different, and each represents a hydrogen atom, an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, a heterocyclic group that may have at least one substituent, an alkoxy group that may have at least one substituent, an aryloxy group that may have at least one substituent, a monoalkylamino group that may have at least one substituent, a dialkylamino group that may have at least one substituent, an acyl group, or an acylamino group. Alternately, $R^{3c}$ and $R^{3d}$ taken together with the adjacent carbon atom may form a saturated or unsaturated aliphatic 4- to 7-membered ring that may have at least one substituent. (The ring may be substituted with at least one member selected from the group consisting of a halogen atom, an oxo group, an alkyl group that may have at least one substituent, an aralkyl group that may have at least one substituent, an aryl group that may have at least one substituent, an alkenyl group that may have at least one substituent, a cyano group, and an amino group.)) Examples of sulfide compounds include methyl ethyl sulfide, methyl benzyl sulfide, 2-phenylthioacetate, 2-phenylthioacetophenone, 2-(methylthio) acetophenone, bis(methylthio)methylbenzene, 2-octyl-1,3-dithiane, 2-phenyl-2-trifluoromethyl-1,3-dithiolane, tris(ethylthio)hexane, 4-tris(methylthio)toluene, and the like.

(4) Fluorination of Olefin Compounds or Epoxy Compounds

In this fluorination, the following fluorine addition reaction, for example, is conducted.

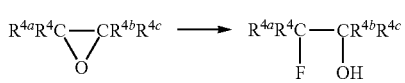

(In the above formula, $R^4$, $R^{4a}$, $R^{4b}$, and $R^{4c}$ may be the same or different, and each represents a hydrogen atom, an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, or a heterocyclic group that may have at least one substituent).

Examples of olefines include tetrafluoroethylene, methyl acrylate, methyl methacrylate, and the like.

Examples of epoxy compounds include oxirane, 1,2-epoxyethylbenzene, 1-chloro-2,3-epoxypropane, α,α'-epoxybibenzyl, and the like.

(5) Fluorination of Aromatic Compounds

In this fluorination, a fluorine substituent is introduced into an aromatic ring by, for example, the following reaction. The target fluorine compound is obtained by fluorination of an aromatic ring in a phenol derivative or aniline derivative, followed by reduction using zinc powder or like reducing agents.

(5-1) Fluorination of Phenylhydrazine Derivatives

A phenylhydrazine residue that may have at least one substituent can be substituted with a fluorine atom.

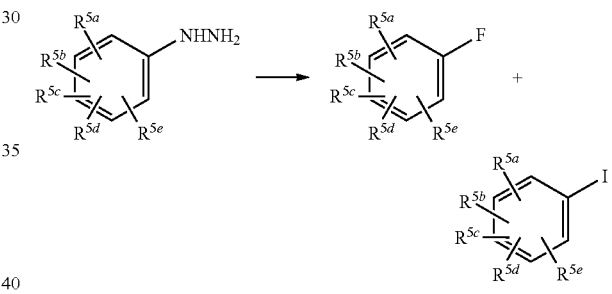

(In the above formula, $R^{5a}$, $R^{5b}$, $R^{5d}$, and $R^{5e}$ may be the same or different, and each represents a hydrogen atom, an alkyl group, an aralkyl group, an aryl group, an alkoxy group, a nitro group, a cyano group, a halogen atom, an alkanoyl group, an arylcarbonyl group, an amino group, a monoalkylamino group, a dialkylamino group, an alkanoylamino group, an arylcarbonyl amino group, or an alkylthio group).

(5-2) Fluorination of phenol Derivatives

A phenol derivative forms the following difluorinated quinonoid structure by reacting with $IF_5$. Thereafter, by reducing the resulting compound, a phenol derivative having fluorine introduced into the ortho- or para-position is produced.

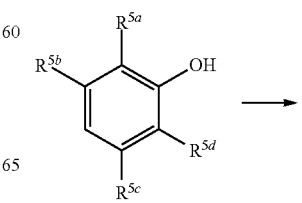

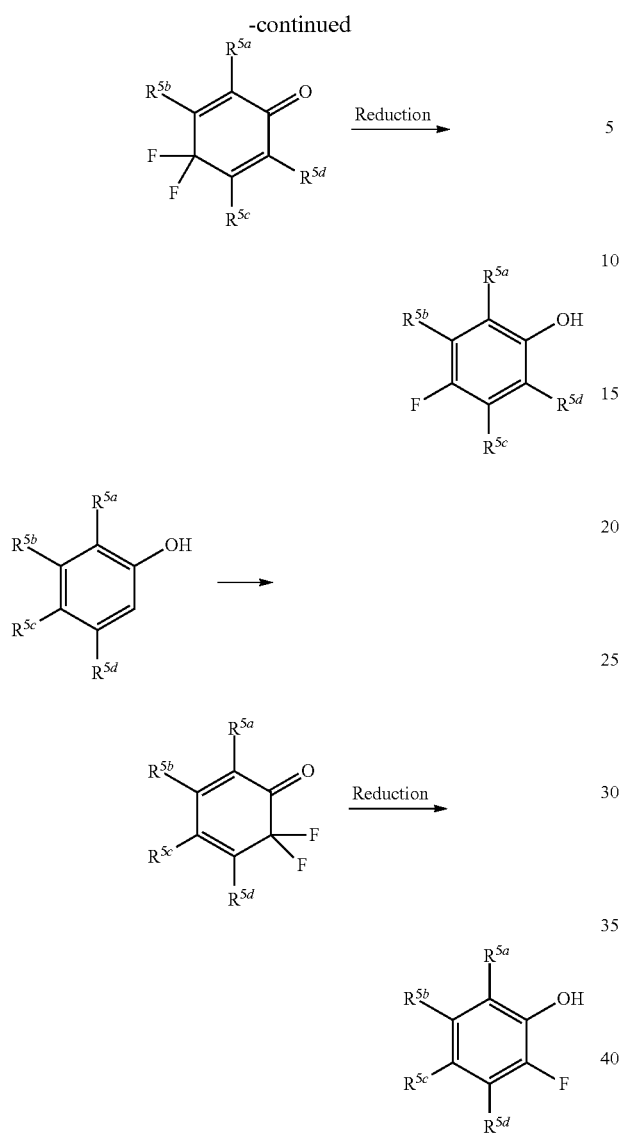

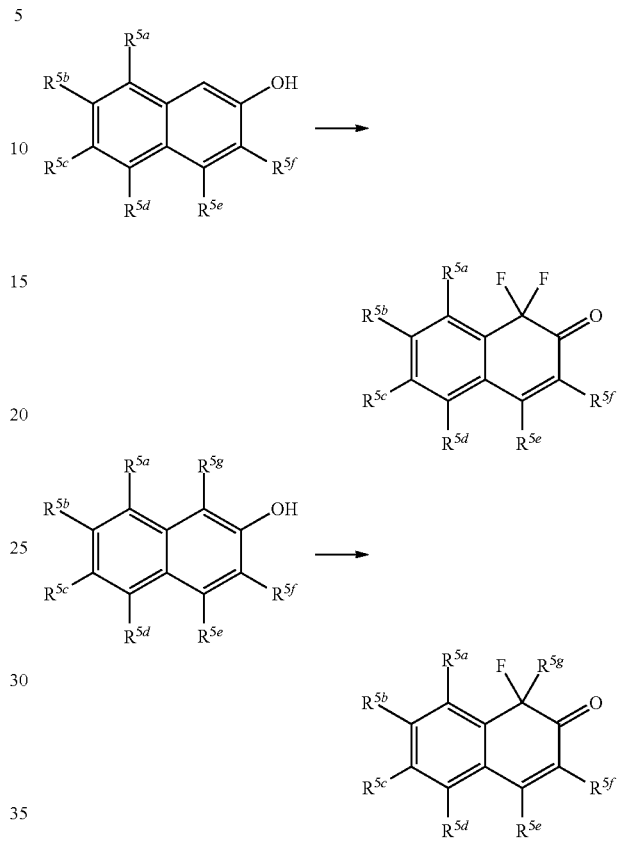

(In the above formulae, $R^{5a}$, $R^{5b}$, $R^{5c}$, and $R^{5d}$ may be the same or different, and each represents a hydrogen atom, an alkyl group, an aralkyl group, an aryl group, an alkoxy group, a nitro group, a cyano group, a halogen atom, an alkanoyl group, an arylcarbonyl group, an amino group, a monoalkylamino group, a dialkylamino group, an alkanoylamino group, an arylcarbonyl amino group, or an alkylthio group).

In a starting material in which all atoms or groups in the ortho- and para-positions are substituted, fluorine atoms are introduced into the ortho- or para-position, forming compounds having a fluorinated quinonoid structure.

In the above example, phenol that may have at least one substituent is used as a phenol derivative; however, it is also possible to introduce fluorine atoms into benzene-based aromatic compounds or condensed polycyclic hydrocarbons that may be substituted and have electron-releasing groups such as a hydroxyl group or an alkoxy group.

(5-3) Fluorination of 2-naphthol Derivatives

A carbon atom in the 1-position of naphthol can be subjected to mono- or difluorination.

(In the above formulae, $R^{5a}$, $R^{5b}$, $R^{5c}$, $R^{5d}$, $R^{5e}$, $R^{5f}$, and $R^{5g}$ may be the same or different, and each represents a hydrogen atom, an alkyl group, an aralkyl group, an aryl group, an alkoxy group, a nitro group, a cyano group, a halogen atom, an alkanoyl group, an arylcarbonyl group, an amino group, a monoalkylamino group, a dialkylamino group, an alkanoylamino group, an arylcarbonyl amino group, or an alkylthio group).

(5-4) Fluorination of Aniline Derivatives

Similar to a phenol derivative, an aniline derivative also forms the following difluorinated quinonoid structure by reacting with $IF_5$. Then, by reducing the resulting compound, an aniline derivative having fluorine introduced into the ortho- or para-position is produced.

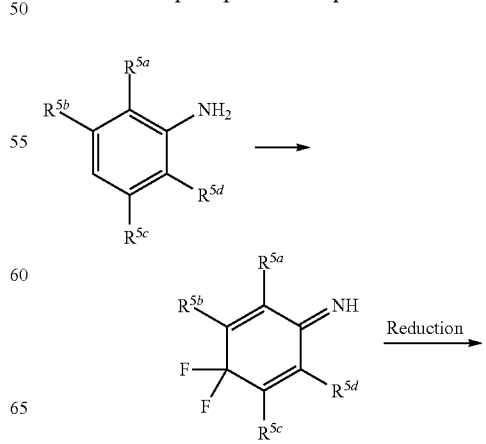

-continued

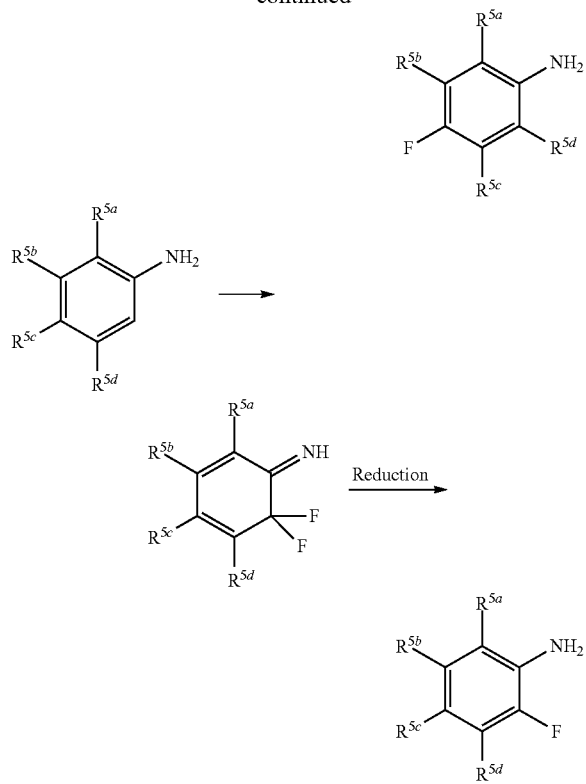

(In the above formulae, $R^{5a}$, $R^{5b}$, $R^{5c}$, and $R^{5d}$ may be the same or different, and each represents a hydrogen atom, an alkyl group, an aralkyl group, an aryl group, an alkoxy group, a nitro group, a cyano group, a halogen atom, an alkanoyl group, an arylcarbonyl group, an amino group, a monoalkylamino group, a dialkylamino group, an alkanoylamino group, an arylcarbonyl amino group, or an alkylthio group).

Using aniline that may have at least one substituent or naphthylamine that may have at least one substituent as an aniline derivative also allows a fluorine atom to be introduced into an aromatic ring.

(6) Fluorination of Thiocarbonyl Compounds (Including Thioketone, Thioester, Thiocarbonic Ester, Thioamide, Cithiocarboxylate, and Dithiocarbamate)
The following reactions are conducted.

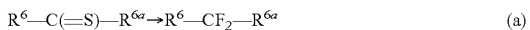 (a)

 (b)

(In the above formulae, $R^6$ and $R^{6a}$ may be the same or different, and each represents a hydrogen atom, an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, a heterocyclic group that may have at least one substituent, an alkoxy group that may have at least one substituent, an aryloxy group that may have at least one substituent, a monoalkylamino group that may have at least one substituent, a dialkylamino group that may have at least one substituent, an acyl group, or an acylamino group. $R^6$ and $R^{6a}$ taken together may form a ring structure. $R^{6b}$ represents an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, or a heterocyclic group that may have at least one substituent).

Examples of thiocarbonyl compounds include O-(4-isopropylphenyl) S-methyl dithiocarbonate, O-(4-bromophenyl)S-methyl dithiocarbonate, ethyl 4-(((methylthio) carbonothioyl)oxy) benzoate, O-decyl S-methyl dithiocarbonate, O-(3-phenylpropyl)S-methyl dithiocarbonate, O-methyl cyclohexanecarbothioate, O-propyl 1-piperidinecarbothioate, methyl dithiobenzoate, thiobenzophenone, O-phenyl thiobenzoate, N,N-dimethylphenylthioamide, ethyl 3-quinolinedithiocarboxylate, trifluoromethane carbothioyl naphthalene, N-methyl-N-phenyl trifluoromethanethioamide, N-benzyl-N-phenylheptafluoropropane thioamide, O-(4'-pentyl-[1,1'-bi(cyclohexan)]-4-yl)S-methyl dithiocarbonate, and the like.

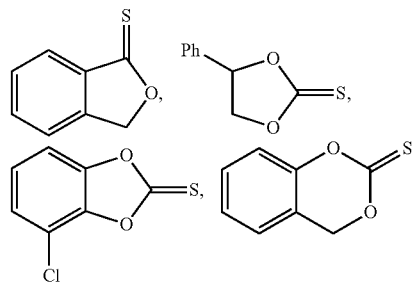

(7) Polyfluorination of Ethyl Moiety of —COOR Group-Containing Ethylsulfides
In this fluorination, the ethyl moiety adjacent to a sulfur atom is polyfluorinated.

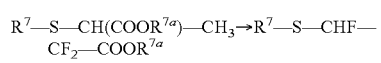

(In the above formula, $R^7$ represents an aryl group that may have at least one substituent or an aromatic heterocyclic group that may have at least one substituent. $R^{7a}$ represents a hydrogen atom, an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, a heterocyclic group that may have at least one substituent, an alkoxy group that may have at least one substituent, an aryloxy group that may have at least one substituent, an amino group, a monoalkylamino group that may have at least one substituent, a dialkylamino group that may have at least one substituent, an acyl group, an acylamino group, a cyano group, an alkylsulfinyl group that may have at least one substituent, an aralkylsulfinyl group that may have at least one substituent, an arylsulfinyl group that may have at least one substituent, a cycloalkylsulfinyl group that may have at least one substituent, a heterocycloalkylsulfinyl group that may have at least one substituent, a sulfinyl group bonded by a heterocyclic group that may have at least one substituent, an alkylsulfonyl group that may have at least one substituent, an aralkylsulfonyl group that may have at least one substituent, an arylsulfonyl group that may have at least one substituent, a cycloalkylsulfonyl group that may have at least one substituent, a heterocycloalkylsulfonyl group that may have at least one substituent, or a sulfonyl group bonded by a heterocyclic group that may have at least one substituent).

Examples of —COOR group-containing ethylsulfides include 2-((4-chlorophenyl)thio)ethyl propanate, and the like.

(8) Fluorination of Unsaturated Carbon Compounds

In this fluorination, fluorine or iodine is added to a carbon-carbon double bond or carbon-carbon triple bond.

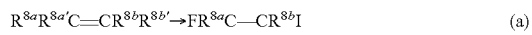  (a)

  (b)

(In the above formulae, $R^{8a}$, $R^{8a'}$, $R^{8b}$, and $R^{8b'}$ may be the same or different, and each represents a hydrogen atom, an alkyl group that may have at least one substituent, an aryl group that may have at least one substituent, an aralkyl group that may have at least one substituent, an alkenyl group that may have at least one substituent, an acyl group, a cycloalkyl group that may have at least one substituent, a neterocycloalkyl group that may have at least one substituent, an ester group, or a halogen atom. At least two of $R^{8a}$, $R^{8a'}$, $R^{8b}$ and $R^{8b'}$ taken together may form a ring structure.)

Examples of the ring structure include aliphatic 4- to 12-membered rings that may have at least one substituent, and the like.

Examples of the unsaturated carbon compound include $C_{2-20}$ unsaturated carbon compounds, such as decene, cyclododecene, and dodecyne.

Examples of alkyl groups include methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, and like straight or branched $C_{1-18}$ alkyl groups. Preferable examples include methyl, ethyl, n-propyl, isopropyl, n-butyl, isobutyl, sec-butyl, tert-butyl, pentyl, hexyl, and like straight or branched $C_{1-6}$ alkyl groups.

Examples of alkoxy groups include methoxy, ethoxy, n-propoxy, isopropoxy, n-butoxy, isobutoxy, sec-butoxy, test-butoxy, pentyloxy, hexyloxy, and like straight or branched $C_{1-6}$ alkoxy groups.

Examples of alkenyl groups include a vinyl group, an allyl group, a 3-butenyl group, and like $C_{2-6}$ alkenyl groups, etc.

Examples of halogens include a fluorine atom, a chlorine atom, a bromine atom, and an iodine atom.

Examples of aryl groups include a phenyl group, a naphthyl group, and the like.

Examples of aryloxy groups include a phenoxy group, a naphthyloxy group, and the like.

Examples of aralkyl groups include 2-phenylethyl, benzyl, 1-phenylethy, 3-phenylpropyl, 4-phenylbutyl, and like $C_{7-10}$ aralkyl groups, etc.

Examples of cycloalkyl groups include cyclopropyl, cyclobutyl, cyclopentyl, cyclohexyl, cycloheptyl, cyclooctyl, and like $C_{3-8}$ cycloalkyl groups, etc., with $C_{3-7}$ cycloalkyl groups being preferable.

Examples of heterocycloalkyl groups include substances in which one or more ring-constituting carbon atoms of the cycloalkyl groups mentioned above are replaced with nitrogen, oxygen, sulfur, and the like.

Examples of monoalkylamino groups include amino groups monosubstituted with the $C_{1-6}$ alkyl groups mentioned above.

Examples of dialkylamino groups include dimethylamino, diethylamino, di-n-propylamino, diisopropylamino, dibutylamino, dipentylamino, dihexylamino, and like amino groups di-substituted with the $C_{1-6}$ alkyl groups mentioned above.

Examples of acylamino groups include formylamino, benzoylamino, acetylamino, propionylamino, n-butyrylamino, and like $C_{1-8}$ acylamino groups (e.g., formylamino, alkanoylamino, and arylcarbonylamino).

Examples of alkylthio groups include —S—($C_{1-6}$alkyl groups), and the like ($C_{1-6}$ alkyl groups are the same as described above).

Examples of heterocyclic groups include piperidyl, furyl, thienyl, imidazolyl, oxazolyl, triazolyl, pyrrolyl, pyrrolidinyl, triazolyl, benzothiazolyl, benzoimidazolyl, oxadiazolyl, thiadiazolyl, indolyl, pyrazolyl, pyridazinyl, cinnolinyl, quinolyl, isoquinolyl, quinoxalinyl, pyradinyl, pyridyl, benzofuryl, benzothienyl, tetrazolyl, and like 5- to 10-membered monocyclic or bicyclic heterocyclic groups having at least one hetero atom selected from nitrogen, oxygen, and sulfur as a ring constituting atom.

Of the heterocyclic groups, examples of aromatic heterocyclic groups include furyl, thienyl, imidazolyl, oxazolyl, triazolyl, pyrrolyl, triazolyl, benzothiazolyl, benzoimidazolyl, oxadiazolyl, thiadiazolyl, indolyl, pyrazolyl, pyridazinyl, cinnolinyl, quinolyl, isoquinolinyl, quinoxalinyl, pyradinyl, pyridyl, benzofuryl, benzothienyl, tetrazolyl, and like 5- to 10-membered monocyclic or bicyclic heteroaryl groups having at least one hetero atom selected from nitrogen, oxygen, and sulfur as a ring constituting atom.

Examples of acyl groups include a formyl group; acetyl, propionyl, n-butyryl, isobutyryl, valeryl, isovaleryl, pivaloyl, and like straight or branched $C_{2-6}$ alkanoyl groups; and benzoyl and like $C_{7-15}$ arylcarbonyl groups.

Specific examples of an alkyl group, an aralkyl group, an aryl group, a cycloalkyl group, a heterocycloalkyl group, and a heterocyclic group in an alkylsulfinyl group, an aralkylsulfinyl group, an arylsulfinyl group, a cycloalkylsulfinyl group, a heterocycloalkylsulfinyl group, and a sulfinyl group having a heterocyclic group bonded thereto are as described above.

Specific examples of an alkyl group, an aralkyl group, an aryl group, a cycloalkyl group, a heterocycloalkyl group, and a heterocyclic group in an alkylsulfonyl group, an aralkylsulfonyl group, an arylsulfonyl group, a cycloalkylsulfonyl group, a heterocycloalkylsulfonyl group, and a sulfonyl group having a heterocyclic group bonded thereto are as described above.

Examples of esters include an acyl-O-group and an alkoxy-CO-group. Here, the "acyl" or "alkoxy" may be, for example, the acyl groups or alkoxy groups mentioned above.

The number of substituents in an alkyl group having at least one substituent, an alkoxy group having at least one substituent, or an alkenyl group having at least one substituent is 1 to 5, and preferably 1 to 3. Examples of the substituent include halogen, $C_{1-6}$ alkoxy, $C_{1-6}$alkylthio, cyano, nitro, an amino group, a hydroxyl group, and the like. Examples of an alkyl group having a halogen include an alkyl group in which a part or all of the hydrogen atoms are substituted with fluorine.

The number of substituents in an aralkyl group having at least one substituent, an aryl group having at least one substituent, an aryloxy group having at least one substituent, a cycloalkyl group having at least one substituent, a heterocycloalkyl group having at least one substituent, a heterocyclic group having at least one substituent, a monoalkylamino group having at least one substituent, a dialkylamino group having at least one substituent, an acylamino group, an alkylsulfinyl group having at least one substituent, an aralkylsulfinyl group having at least one substituent, an arylsulfinyl group having at least one substituent, a cycloalkylsulfinyl group having at least one substituent, a heterocycloalkylsulfinyl group having at least one substituent, a sulfinyl group bonded by a heterocyclic group that may have at least one substituent, an alkylsulfonyl group having at least one substituent, an aralkylsulfonyl group having at least one substituent, an arylsulfonyl group having at least one substituent, a cycloalkylsulfonyl group having at least one substituent, a heterocycloalkylsulfonyl group having at least one substituent, or a sulfonyl group bonded by a heterocyclic group having at least one substituent is 1 to 5, and preferably 1 to 3. Examples of the substituent include $C_{1-6}$ alkyl groups, halogen atoms, $C_{1-6}$ alkoxy groups, $C_{1-6}$alkylthio, cyano, nitro, an amino group, a hydroxyl group, and the like.

The number of substituents in aliphatic 4- to 7-membered rings having at least one substituent is 1 to 5, and preferably 1 to 3. Examples of substituents include $C_{1-6}$ alkyl groups, halogen atoms, $C_{1-6}$alkoxy groups, $C_{1-6}$alkylthio, cyano, nitro, an amino group, a hydroxyl group, carboxy esters, and the like. In addition,

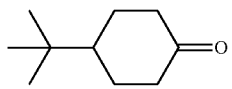

is also included in the aliphatic 4- to 7-membered rings having at least one substituent.

Examples of acyl groups include a chloroacetyl group, bromoacetyl group, dichloroacetyl group, trifluoroacetyl group, and like substituted acetyl groups; a methoxyacetyl group, ethoxyacetyl group, and like alkoxy-substituted acetyl groups; a methylthioacetyl group and like alkylthio-substituted acetyl groups; a phenoxyacetyl group, phenylthioacetyl group, 2-chlorobenzoyl group, 3-chlorobenzoyl group, 4-chlorobenzoyl group, 4-methylbenzoyl group, 4-t-butylbenzoyl group, 4-methoxybenzoyl group, 4-cyanobenzoyl group, 4-nitrobenzoyl group, and like substituted benzoyl groups, etc.

The composition of the present invention is suitably used in Step A such that the amount of the $IF_5$ is within a range of 0.2 to 10 mol per mol of the moiety subjected to fluorination of the organic compound, which is a substrate. More specifically, for example, the amount of the $IF_5$-pyridine-HF is preferably in a range of 0.2 to 10 mol, more preferably 0.5 to 5 mol, and even more preferably 0.5 to 3 mol, per mol of the organic compound, which is a starting compound.

Step A in the production method for the present invention can be suitably performed in air. The air may be ordinary air that has not been dried. Accordingly, the production method for the present invention can be performed at low cost, and is industrially advantageous.

The reaction temperature of Step A in the production method for the present invention is generally in a range of −100 to 140° C., preferably in a range of −20 to 120° C., and more preferably in a range of 0 to 100° C.

The reaction time of Step A in the production method for the present invention is generally in a range of 0.5 to 48 hours, preferably in a range of 1 to 24 hours, and more preferably in a range of 2 to 24 hours.

The production method for the present invention is suitably performed in the presence of a reaction solvent.

Examples of the reaction solvent may be the same as the examples of the aprotic solvent contained in the composition of the present invention.

Examples of the reaction solvent include methylene chloride, dichloroethane, tetrachloroethane, chloroform, cyclohexane, and mixed solvents of two or more of these.

The amount of the reaction solvent used in Step A is preferably in a range of 0 to 50 parts by mass, and more preferably in a range of 5 to 30 parts by mass, per part by mass of the organic compound as a starting compound.

The production method for the present invention can be carried out in air by adding an organic compound having at least one hydrogen atom t₀a reactor containing a reaction solvent and the composition of the present invention.

The fluorinated organic compound produced by the production method for the present invention can be generated by a known method, such as extraction.

Advantageous Effects of Invention

According to the composition, fluorinating reagent, or production method for the present invention, a fluorinated organic compound is obtained with a high yield that has not been produced with a sufficient yield by a known method that uses a fluorinating agent containing $IF_5$-pyridine-HF alone.

Examples of the fluorinated organic compounds that have not been produced with a sufficient yield by a known method include compounds with a larger fluorine amount. Specific examples of such compounds include
trifluoromethyl 4-isopropyl phenyl ether,
1-bromo-4-(trifluoromethoxy)benzene,
ethyl 4-(trifluoromethoxy)benzoate,
1-(trifluoromethoxy)decane,
(3-(trifluoromethoxy)propyl)benzene,
ethyl 3-((4-chlorophenyl)thio)-2,2,3-trifluoropropanate,
4-pentyl-4'-(trifluoromethoxy)-1,1'-bi(cyclohexane),
1-fluoro-2-iodocyclododecane,
5-fluoro-6-iododecane, and
(Z)-2-fluoro-1-iodododecan-1-ene.

EXAMPLES

The present invention is described below in further detail. However, the present invention is not limited to these Examples.

In the Examples, the unit "ppm" refers to mass ppm, unless otherwise specified.

The following is the meaning of the symbol used in the Examples.
pen: Pentyl

In each Example, the amount of cyclohexane residue was measured according to the following measurement method.
Measurement Method
i) Accurately weigh about 50 to 150 mg of a sample composition;
ii) Add 4 ml of 0.1N KOH aqueous solution;
iii) Add 2 ml of toluene;
iv) Stir the mixture for 5 minutes, and allow the resulting mixture to stand for 10 minutes;
v) Subject the cyclohexane residue in the toluene layer to GC measurement; and
vi) Calculate the amount of cyclohexane residue, based on the calibration curve value. The average value obtained with n=3 is considered the amount of cyclohexane residue. The "amount of cyclohexane residue" as used herein means the amount of cyclohexane contained in the sample composition, i.e., (mass of cyclohexane)/(mass of the sample composition).

Production Example 1

IF$_5$ (45 g, 0.20 mol) was placed in a container, to which 200 ml of cyclohexane was added at 0° C., followed by further addition of pyridine-HF (pyridine 50 mol %, HF 50 mol %) (20 g, 0.20 mol each). The resulting mixture was stirred for 30 minutes at 0° C., and then left to stand at room temperature for 1 hour to thus obtain a solid containing IF$_5$-pyridine-HF and cyclohexane.

The obtained solid was dried under reduced pressure while varying the conditions for drying under pressure. In this manner, solid compositions containing IF$_5$-pyridine-HF and cyclohexane were obtained with various cyclohexane amounts. Hereinafter, these solid compositions are referred to as IF$_5$-pyridine-HF, and its cyclohexane content is referred to as the amount of cyclohexane residue.

Example 1

Fluorination Reaction Test

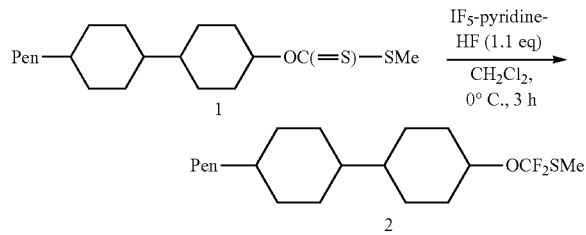

IF$_5$-pyridine-HF (1.1 mmol) (the amount of cyclohexane residue: 202 mass ppm) and dichloromethane (2.0 mL) were placed in a reactor with a lid, to which substrate 1 (1.0 mmol) was added, and the mixture was allowed to react at 0° C. for 3 hours.

After purification, an internal standard (hexafluorobenzene) was added to the residue, and the product was quantified by $^{19}$F-NMR. The results indicate that difluoro body 2 was produced with a yield of 60%.

Comparative Example 1

Fluorination Reaction Test

IF$_5$-pyridine-HF (1.1 mmol) (the amount of cyclohexane residue: 43 mass ppm) and dichloromethane (2.0 mL) were placed in a reactor with a lid, to which substrate 1 (1.0 mmol) was added at room temperature, and the mixture was allowed to react at 0° C. for 3 hours. After purification, an internal standard (hexafluorobenzene) was added to the residue, and the product was quantified by $^{19}$F-NMR. As a result, difluoro body 2 was not detected, and the yield was 0%, indicating that difluoro body 2 was not produced.

Test Example 1

Fluorination Reaction Test

Table 1 shows the results of the fluorination reaction test performed with respect to the samples of each product produced as in Example 1 and Comparative Example 1, using IF$_5$-pyridine-HF with various amounts of cyclohexane residue (Examples 1 to 4 and Comparative Examples 1 and 2). As is clear from the results, the use of the composition of the present invention allows the fluorination reaction to proceed to thus yield the target product.

TABLE 1

| | No. | | | | | |
|---|---|---|---|---|---|---|
| | 1 (Ex. 2) | 2 (Ex. 1) | 3 (Ex. 3) | 4 (Ex. 4) | 5 (Comp. Ex. 1) | 6 (Comp. Ex. 2) |
| Amount of cyclohexane residue | 19 mass % | 202 ppm | 99 ppm | 87 ppm | 43 ppm | 33 ppm |
| Fluorination reaction | + | + | + | + | n.d. | n.d. |

+: The fluorinated reaction product (difluoro body 2) was detected.
n.d.: The fluorinated reaction product (difluoro body 2) was not detected.

The invention claimed is:

1. A solid composition comprising:
   (1) IF$_5$-pyridine-HF and
   (2) at least one aprotic solvent selected from the group consisting of (cyclo)alkanes, aromatic solvents, and fluorine-containing organic solvents, wherein
   the aprotic solvent is contained in the solid composition in an amount within a range of 50 mass ppm to 20 mass %.

2. The solid composition according to claim 1, wherein the aprotic solvent is at least one member selected from the group consisting of C$_{1-10}$(cyclo)alkanes, and C$_{1-7}$ fluorine-containing organic solvents.

3. The solid composition according to claim 1, wherein the aprotic solvent is a C$_{1-10}$(cyclo)alkane.

4. The solid composition according to claim 1, wherein the aprotic solvent is cyclohexane.

5. The solid composition according to claim 1, which is a fluorinating reagent.

6. A method for producing a fluorinated organic compound,
   the method comprising Step A of fluorinating an organic compound by bringing the organic compound into contact with the solid composition of claim 1.

7. The solid composition according to claim 2, which is a fluorinating reagent.

8. The solid composition according to claim 3, which is a fluorinating reagent.

9. The solid composition according to claim 4, which is a fluorinating reagent.

10. A method for producing a fluorinated organic compound, the method comprising Step A of fluorinating an organic compound by bringing the organic compound into contact with the solid composition of claim 2.

11. A method for producing a fluorinated organic compound, the method comprising Step A of fluorinating an organic compound by bringing the organic compound into contact with the solid composition of claim 3.

12. A method for producing a fluorinated organic compound, the method comprising Step A of fluorinating an organic compound by bringing the organic compound into contact with the solid composition of claim 4.

13. A method for producing a fluorinated organic compound, the method comprising Step A of fluorinating an organic compound by bringing the organic compound into contact with the solid composition of claim 5.

14. A method for producing a fluorinated organic compound, the method comprising Step A of fluorinating an organic compound by bringing the organic compound into contact with the solid composition of claim 7.

15. A method for producing a fluorinated organic compound, the method comprising Step A of fluorinating an organic compound by bringing the organic compound into contact with the solid composition of claim 8.

16. A method for producing a fluorinated organic compound, the method comprising Step A of fluorinating an organic compound by bringing the organic compound into contact with the solid composition of claim 9.

\* \* \* \* \*